United States Patent [19]
Wheeler et al.

[11] Patent Number: 5,856,329
[45] Date of Patent: Jan. 5, 1999

[54] METHOD OF USING (2-IMIDAZOLIN-2-YLAMINO) QUINOXALINES IN TREATING OCULAR NEURAL INJURY

[75] Inventors: Larry A. Wheeler, Irvine; Elizabeth Woldemussie, Laguna Niguel; Ronald K. Lai, Santa Ana, all of Calif.

[73] Assignee: Allergan, Waco, Tex.

[21] Appl. No.: 496,262

[22] Filed: Jun. 28, 1995

[51] Int. Cl.$^6$ .................................................. A61K 31/495
[52] U.S. Cl. ........................................... 514/255; 514/912
[58] Field of Search ..................................... 514/255, 912

[56] References Cited

U.S. PATENT DOCUMENTS

| | | |
|---|---|---|
| 4,029,792 | 6/1977 | Danielewicz et al. . |
| 5,180,721 | 1/1993 | Burke . |
| 5,215,991 | 6/1993 | Burke . |

FOREIGN PATENT DOCUMENTS

| | | |
|---|---|---|
| 0 422 878 A1 | 10/1990 | European Pat. Off. . |
| 0 426 390 A2 | 10/1990 | European Pat. Off. . |
| PCT/US95/ 13624 | 10/1995 | WIPO . |

OTHER PUBLICATIONS

Schumer et al, "The Nerve of Glaucoma!", Arch. Ophthalmol. vol. 112, Jan. 1994, pp. 37–44.

Barnebey et al., "The Efficacy of Brimonidine in Decreasing Elevations in Intraocular Pressure after Laser Trabeculoplasty", Ophthalmology, 100(7) Jul. 1993, 1083–1088.

David, et al., "Brimonidine in the Prevention of Intraocular Pressure Elevation Following Argon Laser Trabeculoplasty", Arch Ophthalmol, vol. 111, Oct. 1993, 1287–1390.

Janet B. Serle, "Pharmacological Advances in the Treatment of Glaucoma", Drugs Aging, 5 (3), Sep. 1994, 156–170.

E. Yales, et al., "Injury–Induced Secondary Degeneration of Rat Optic Nerve Can Be Attenuated by α2/Adrenoceptor Agonists AGN 191103 and Brimonidine" Investigative Ophthalmology and Visual Science, 37 (3), 1996, S114.

Sabel et al, "Functional Recovery and Morphological Changes after Injury to the Optic Nerve", Neuropsychobiology 1993; 28: 62–65.

Stys et al, "Compound action potential of nerve recorded by suction electrode: a theoretical and experimental analysis", Brain Research, 546 (1991) pp. 18–32.

Burke et al, "Ocular effects of a relatively selective α2 agonist (UK–14, 304–18) in cats, rabbits and monkeys", Current Eye Research, vol. 5, No. 9, 1986, pp. 665–676.

Michel et al, "Keeping an eye on the I site: imidazoline–preferring receptors", TiPS—Oct. 1992 [vol. 13], pp. 369–370.

Chemical Abstracts 122: 96456 (1994). Gablet et al.

Primary Examiner—Zohreh Fay
Attorney, Agent, or Firm—James M. Hoch; Robert J. Baran; Martin A. Voet

[57] ABSTRACT

A method according to which neuroprotection is conferred upon ocular nerve cells by administration of a drug of formula I to the optic nerve and/or retina of a mammal within a period prior to or following an insult to ocular nerve cells but prior to cell death

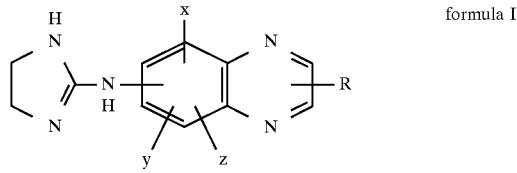

wherein the 2-imidazolin-2-ylamino group may be in either the 5- or 6-position of the quinoxaline nucleus; x, y and z may be in any of the remaining 5-, 6-, 7- or 8-positions and are selected from hydrogen, halogen, lower alkyl, lower alkoxy or trifluoromethyl; and R is an optional substitutent in either the 2- or 3-position of the quinoxaline nucleus and may be hydrogen, lower alkyl or lower alkoxy is disclosed.

15 Claims, 2 Drawing Sheets

METHOD OF USING (2-IMIDAZOLIN-2-YLAMINO) QUINOXALINES IN TREATING OCULAR NEURAL INJURY

BACKGROUND OF THE INVENTION

The present invention relates to methods for the protection of the optic nerve and the retina of mammalian eyes from noxious provocations including damage by compressive (mechanical) effects of elevated intraocular pressure caused by glaucoma or other etiologic factors and impaired blood flow to these nerves.

Glaucoma is a disease of the eye characterized by increased intraocular pressure. On the basis of its etiology, glaucoma has been classified as primary or secondary. Further, primary glaucoma in adults may be either chronic open-angle or chronic angle-closure. Secondary glaucoma results from pre-existing ocular diseases such as uveitis, intraocular tumor or enlarged cataract.

The underlying causes of primary glaucoma are not yet well known. Increased intraocular pressure is due to obstruction or aqueous humor outflow. In chronic open-angle glaucoma, the anterior chamber and its anatomic structures appear normal, but drainage of the aqueous humor is impeded. In acute and chronic angle-closure glaucoma, the anterior chamber is shallow, the filtration angle is narrowed and the iris may obstruct the trabecular meshwork at the entrance to the canal of Schlemm. Dilation of the pupil may push the root of the iris forward against the angle or may produce pupillary block and thus precipitate an acute attack of elevated intraocular pressure. Eyes with narrow anterior chamber angles are predisposed to acute angle-closure glaucoma attacks of varying degrees of severity.

Secondary glaucoma is caused by any interference with the flow of aqueous humor from the posterior chamber into the anterior chamber and, subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, ventral retinal vein occlusion, trauma to the eye, operative procedures and intraocular hemorrhage.

Considering all types together, glaucoma occurs in about 2% of all persons over the age of 40 and may be asymptomatic for years before progressing to rapid loss of vision. In cases where surgery is not indicated, topical beta-adrenoceptor antagonists have been the drugs of choice for treating glaucoma. However, alpha adrenergic agonists are awaiting approval for use in the treatment of elevated intraocular pressure and will probably become mainstays in the treatment of this disease once they become available.

Various quinoxaline derivatives having alpha$_2$ agonist activity have been suggested as therapeutic agents by, for example, Danielewicz, et al. in U.S. Pat. Nos. 3,890,319 and 4,029,792. They disclose compounds as regulators of the cardiovascular system which have the following formula:

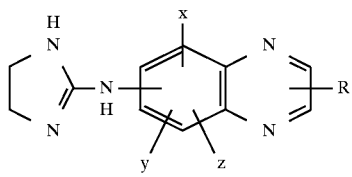

where the 2-imidazolin-2-ylamino group may be in any of the 5-, 6-, 7- or 8-position of the quinoxaline nucleus; x, y and z may be in any of the remaining 5-, 6-, 7- or 8-positions and may be selected from hydrogen, halogen, lower alkyl, lower alkoxy or trifluoromethyl; and R is an optional substituent in either the 2- or 3-position of the quinoxaline nucleus and may be hydrogen, lower alkyl or lower alkoxy. The presently useful compounds may be prepared in accordance with the procedures outlined by Danielewicz, et al. The contents of both U.S. Pat. Nos. 3,890,319 and 4,029,792 are hereby incorporated by reference in their entirety.

In "Ocular Effects of a Relatively Selective Alpha-2 Agonist (UK-14,304-18) in Cats, Rabbits and Monkeys" [J. A. Burke, et al., *Current Eye Rsrch.*, 5, (9), pp. 665–676 (1986)] the quinoxaline derivative was shown to be effective in reducing intraocular pressure in rabbits, cats and monkeys. Compounds in this study were administered topically to the eye of the study animals.

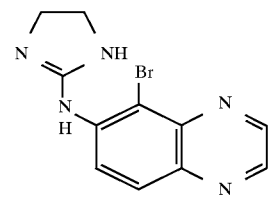

It has long been known that one of the sequelae of glaucoma is damage to the optic nerve head. This damage, referred to as "cupping", results in depressions in areas of the nerve fiber of the optic disk. Loss of sight from this cupping is progressive and can lead to blindness if the condition is not treated effectively.

Unfortunately lowering intraocular pressure by administration of drugs or by surgery to facilitate outflow of the aqueous humor is not always effective in obviating damage to the nerves in glaucomatous conditions. This apparent contradiction is addressed by Cioffi and Van Buskirk [*Surv. of Ophthalmol.*, 38, Suppl. p. S107–16, discussion S116–17, May 1994] in the article, "Microvasculature of the Anterior Optic Nerve". The abstract states:

The traditional definition of glaucoma as a disorder of increased intraocular pressure (IOP) oversimplifies the clinical situation. Some glaucoma patients never have higher than normal IOP and others continue to develop optic nerve damage despite maximal lowering of IOP. Another possible factor in the etiology of glaucoma may be regulation of the regional microvasculature of the anterior optic nerve. One reason to believe that microvascular factors are important is that many microvascular diseases are associated with glaucomatous optic neuropathy.

Subsequent to Cioffi, et al., Matusi published a paper on the "Ophthalmologic aspects of Systemic Vasculitis" [*Nippon Rinsho*, 52 (8), p. 2158–63, August 1994] and added further support to the assertion that many microvascular diseases are associated with glaucomatous optic neuropathy. The summary states:

Ocular findings of systemic vasculitis, such as polyarteritis nodosa, giant cell angitis and aortitis syndrome were reviewed. Systemic lupus erythematosus is not categorized as systemic vasculitis, however its ocular findings are microangiopathic. Therefore, review of its ocular findings was included in this paper. The most common fundus finding in these diseases is ischemic optic neuropathy or retinal vascular occlusions. Therefore several points in diagnosis or pathogenesis of optic neuropathy and retinal and choroidal vaso-occlusion were discussed. Choroidal ischemia has come to be able to be diagnosed clinically, since fluorescein angiography was applied in these lesions. When choroidal arteries are occluded, overlying retinal pigment epithelium is damaged. This causes disruption of barrier function of the epithelium and allows fluid from choroidal vasculatures to pass into subsensory retinal spaces. This is a pathogenesis of serous detachment of the retina. The retinal arterial occlusion formed nonperfused retina. Such hypoxic retina released angiogenesis factors which stimulate retinal and iris neovascularizations and iris neovascularizations may cause neovascular glaucoma.

B. Schwartz, in "Circulatory Defects of the Optic Disk and Retina in Ocular Hypertension and High Pressure Open-Angle Glaucoma" [*Surv. Ophthalmol.*, 38, Suppl. pp. S23–24, May 1994] discusses the measurement of progressive defects in the optic nerve and retina associated with the progression of glaucoma. He states:

Fluorescein defects are significantly correlated with visual field loss and retinal nerve fiber layer loss. The second circulatory defect is a decrease of flow of fluorescein in the retinal vessels, especially the retinal veins, so that the greater the age, diastolic blood pressure, ocular pressure and visual field loss, the less the flow. Both the optic disk and retinal circulation defects occur in untreated ocular hypertensive eyes. These observations indicate that circulatory defects in the optic disk and retina occur in ocular hypertension and open-angle glaucoma and increase with the progression of the disease.

Thus it is evident that there is an unmet need for agents that have neuroprotective effects in the eye that can stop or retard the progressive damage that occurs to the nerves as a result of glaucoma or other ocular afflictions.

SUMMARY OF THE INVENTION

A new method of protecting the optic nerve and retina of the mammalian eye from damage by glaucoma and other noxious provocations has been discovered. This method comprises administering to the mammal either systemically or by intrabulbar injection an effective amount of one or more of certain aryl-imino-2-imidazolidines (as defined herein), salts thereof and mixtures thereof. This new method is particularly effective when administered as a prophylactic treatment, i.e. before damage to the nerve takes place, or before long-term progression of the disease, such as glaucoma, has taken place.

DETAILED DESCRIPTION OF THE INVENTION

The drawings will first be briefly described.

DRAWINGS

Figure 1:
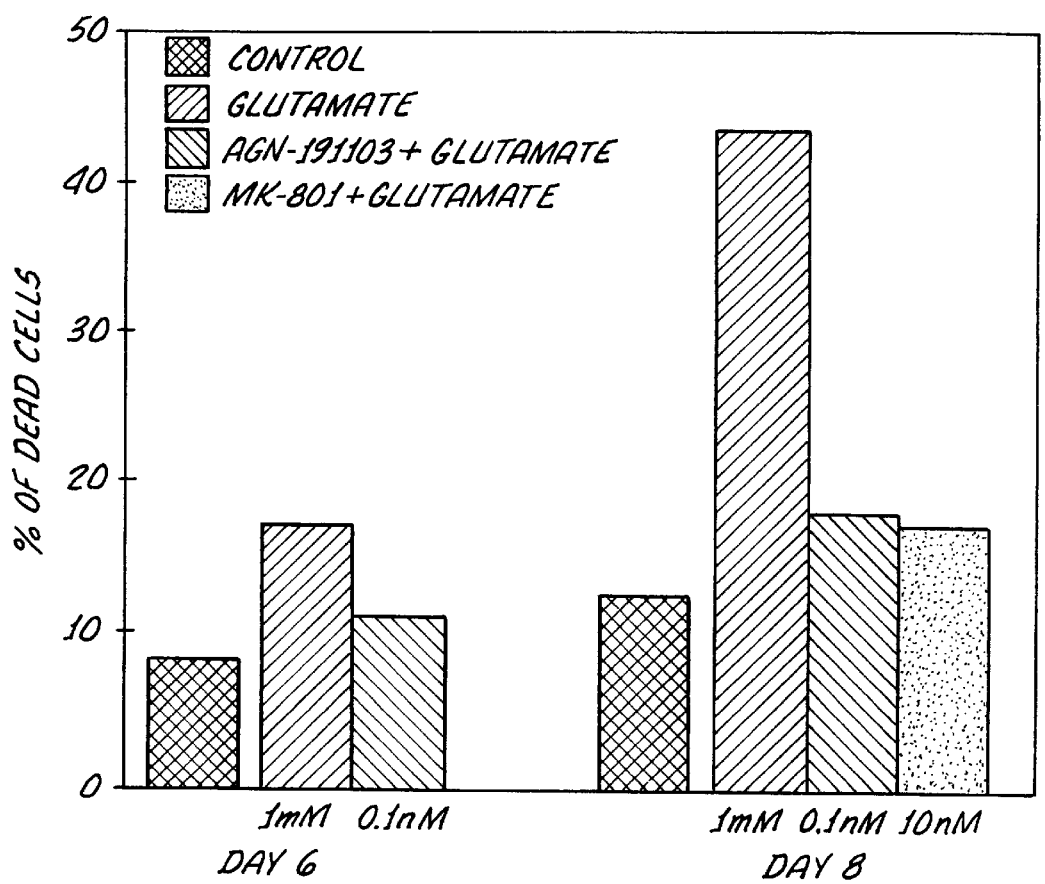

FIG. 1 is a bar graph showing the percentage of cells killed by treatment with glutamate plotted by number of days since glutamate treatment. A control which was not treated with glutamate has been included to determine cell death which occurred without any such treatment. Also shown are measurements taken after treatment with both AGN191103 and glutamate, and treatment with MK-801 and glutamate. MK-801 is a well known neuroprotective agent in the art. The numbers beneath the bars for glutamate; AGN191103+glutamate; and MK-801+glutamate show the concentrations of glutamate and drug used in each case. At day 8, AGN 191103 and MK-801 show comparable effects in protecting cells from glutamate induced neurotoxicity. Experimental procedures followed in generating the data for this figure are detailed in Example 1.

Figure 2:
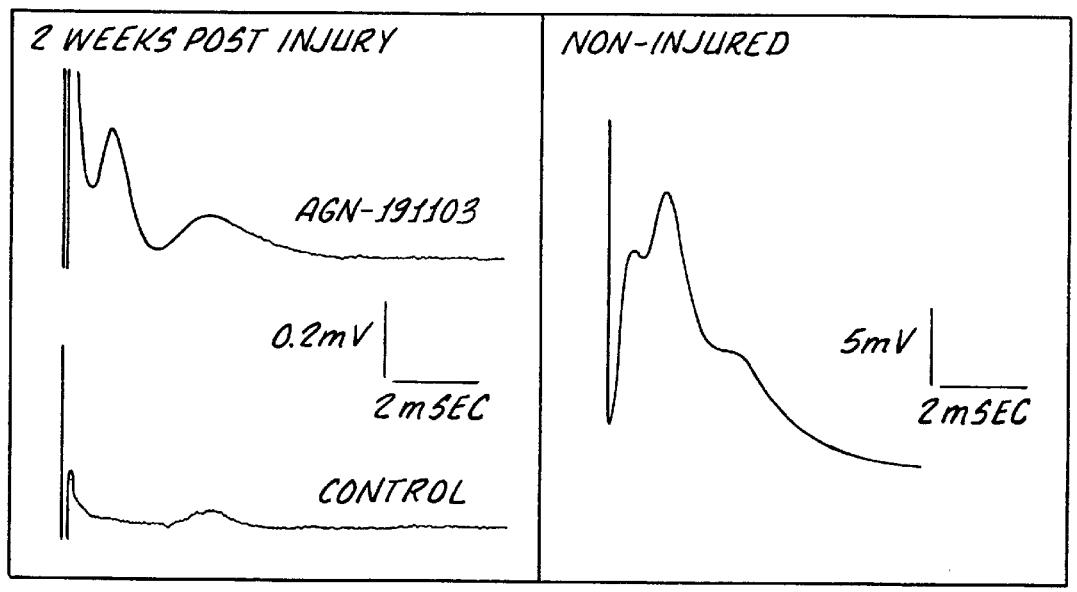

FIG. 2 shows plots of compound action potentials (CAP) measured for optic nerve fibers: in the left-hand frame, measured at 2 weeks post injury (i.e. after nerve crush) for optic nerve treated with AGN 191103 (the upper line) and for an untreated nerve used as a control (lower line); and in the right-hand frame a comparison CAP of non-injured optic nerve. The scales of the plots are given for each of the frames. The post-injury abscissa scale is 25× the scale of the non-injured plot. (Units: millivolts and milliseconds). The value of the compound action potential is calculated as the integral of the area under each curve. The irregularity of the curve is a feature of the dispersion of the compound response; some nerve cells conduct more rapidly than others and so amplitude of the measured voltage varies with time.

Figure 3:
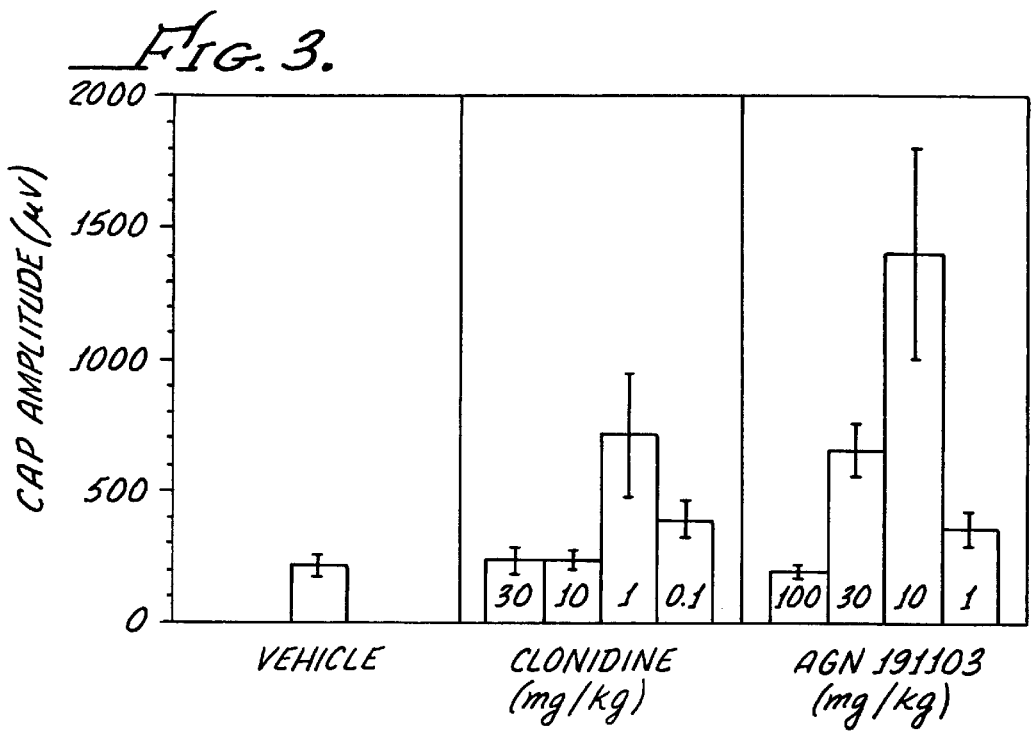

FIG. 3 is a bar graph showing the maximal CAP amplitude in microvolts ($\mu$V) for cells injured by a optic nerve crush in rats and treated with: 1) vehicle alone; 2) clonidine and 3) AGN191103. Each of the drugs was tested at four different concentrations (administered as a multiple of body weight for the test subject) and is represented by a bar on the chart. Clonidine was chosen as a benchmark $\alpha_2$ agonist compound with very well defined pharmacology to compare against the test compound AGN 191103. While clonidine did show some neuroprotective activity over vehicle alone, it showed about half the maximal CAP response of AGN191013.

Figure 4:
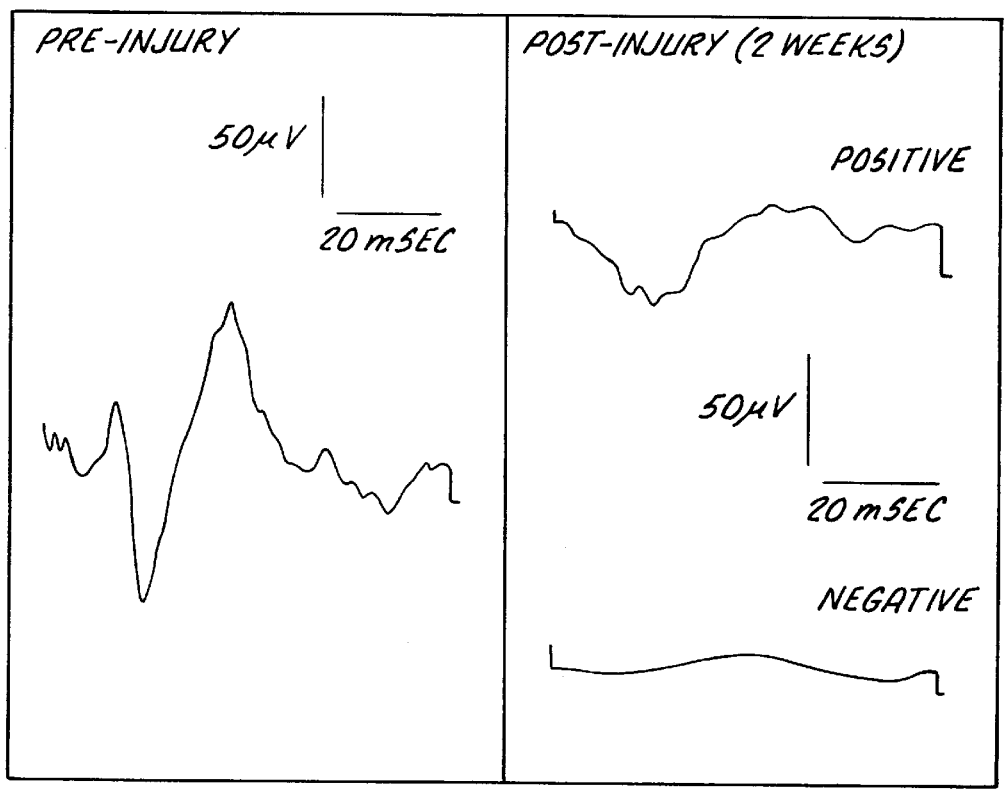

FIG. 4 is a graphic plot of the Visual Evoked Potential Response and shows the electrical potential activity evoked at the surface of the visual cortex (comparable to an electroencephalogram) as a result of visual (light) stimulus. The test is performed in live rats and is a measure of the integrity of the whole visual system from the retina through the optic nerve into the lateral geniculate nucleus and ultimately to the visual cortex located in the back of the brain. The left-hand frame shows the response without nerve crush injury and the right-hand frame shows the responses measured at 2 weeks post-injury for rats treated with AGN191103 above (labeled positive) and control rats below (labeled negative) prior to nerve crush. The scale in $\mu$V vs. milliseconds for both plots is shown below the ordinate axis.

For a discussion and bibliography regarding the nerve crush model and its significance in evaluating nerve damage and recovery see: "Functional Recovery and Morphological Changes after Injury to the Optic Nerve", Sabel, B. A. and Aschoff, A., *Neuropsychobiology*, 28, pp. 62–65 (1993).

Injury to the mammalian optic nerve, as in any other parts of the mammalian central nervous system (CNS), leads to axonal degeneration followed by a loss of cell bodies, with failure of axonal regrowth from the surviving neurons. Initially, degeneration of the injured nerve is probably attributable to direct neuronal damage. However, the associated physiological and biochemical events occurring in the nerve immediately after injury are probably responsible for the subsequent progressive degeneration, not only of the directly injured axons, but also of those that escaped the primary damage and largely determine the long-term functional outcome.

The immediate injury-induced response strongly influences the subsequent degenerative response. Treatment that reduces or attenuates the immediate response is therefore likely to achieve optimal prevention or delay of the secondary degenerative processes. For monitoring of the immediate response, it is obviously preferable to employ a noninvasive technique. An adaptation of the nicotinamide adenine dinucleotide (NADH) monitoring technique to enable measurement of the earliest post-traumatic events has proved to be a valuable non-invasive approach. Use of the technique allows the immediate effect of the injury to be evaluated in real time and on-line before and after a well-controlled crush injury is inflicted on the adult rat optic nerve in vivo. In this experimental paradigm, measurement of the metabolic activity of the injured optic nerves represent the activity of both injured axons and their associated non neuronal cells, and thus evaluate the potential ability to cope with injurious stresses. The model is also useful for monitoring the activity of various agents that may overcome or mitigate nerve cell damage or death from such stresses.

The earliest injury-induced response is a decrease in the energy state of the nerve, under conditions where ischemic events can be completely ruled out. The reduction in the energy state may be related to: 1) postinjury elevation in free fatty acid levels, which may interfere with mitochondrial function and result in uncoupling of electron transport; and 2) a marked rise in intracellular free $Ca^{2+}$. It is known that axonal injury is generally followed by an increase in extracellular potassium ions, which stimulate the uptake of $Ca^{2+}$ via either voltage sensitive channels (L, T or N type) or receptor-operated $Ca^{2+}$ channels. A marked rise in intracellular free $Ca^{2+}$ can accelerate processes that are inimical to cell survival, including those involving $Ca^2$-dependent enzymes, mainly lipases, proteases and endonucleases, that may cause mitochondrial damage and lead eventually to cell death. The cell, in order to overcome these events, needs more energy to actively restore ionic homeostasis. The combination of increased energy demands and decreased energy conservation resulting from mitochondrial dysfunction at the site of injury may be the major reason for the subsequent irreversible nerve damage and nerve degeneration following injury. Early measurement of metabolic activity could therefore indicate the fate of the axon, its associated glial cells and its non-neuronal cell bodies. It follows from the above that restoration of the mitochondrial activity may be critical in preventing the degenerative process occurring in the nerve after injury.

Since the injury inflicted on the nerve in the nerve crush model is a well-controlled, calibrated and reproducible lesion, it is possible to correlate early post-traumatic metabolic deficits and possible mitigation of these by drug or other treatments with long-term morphological and physiological effects.

From the foregoing figures and discussion it is apparent that neuroprotection is conferred on nerve cells to both glutamate-induced toxicity and physical insult in the nerve crush model.

It has now been discovered that neuroprotection is conferred upon ocular nerve cells by administration of a drug of formula I to the optic nerve and/or retina of a mammal within a period prior to or following an insult to ocular nerve cells but prior to cell death

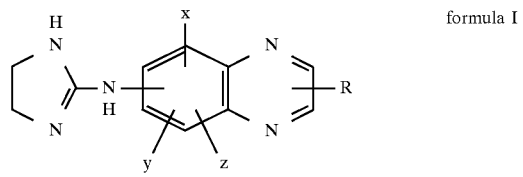

formula I wherein the 2-imidazolin-2-ylamino group may be in either the 5- or 6-position of the quinoxaline nucleus; x, y and z may be in any of the remaining 5-, 6-, 7- or 8-positions and are selected from hydrogen, halogen, lower alkyl, lower alkoxy or trifluoromethyl; and R is an optional substituent in either the 2- or 3-position of the quinoxaline nucleus and may be hydrogen, lower alkyl or lower alkoxy.

Definitions

The compound identified as AGN 191103 has the chemical structure as

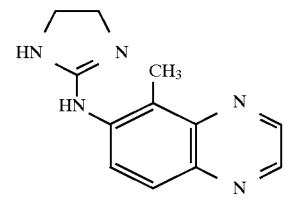

shown. It is also known by the chemical nomenclature 6-methyl-(2-imidazolin-2-ylamino) quinoxaline. The neuroprotective agent identified as MK-801 is also known by the name dizocilpine and has the following chemical structure:

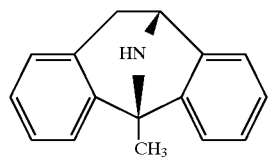

It is additionally identified and described in the 11th edition of the Merck Index at monograph number 3392.

Human Dosage and Administration

The methods of this invention are useful in treating any mammal, including humans.

According to this invention, mammals are treated with pharmaceutically effective amount of a neuroprotective agent for a period of time and at a time such that noxious provocations to the optic nerve and retina do not kill or permanently damage the nerve cells. Protective agents may be administered orally or by any other appropriate means of delivery described below or known in the art.

In accordance with this invention, pharmaceutically effective amounts of a protective agent can be administered alone to treat nerve injury or to prevent nerve cell death. Alternatively a protective agent may be administered sequentially or concurrently with an antiglaucoma drug, e.g. a beta-blocker, an $alpha_2$ agonist, a muscarinic agent such as pilocarpine, a carbonic anhydrase inhibitor (CAI), or another drug useful in maintaining intraocular pressure (IOP) at normal levels or in lowering elevated IOP. The most effective mode of administration and dosage regimen of protective agent will depend on the type of disease to be treated, the severity and course of that disease, previous therapy, the patient's health status, and response to the drug and the judgment of the treating physician. Generally, the neuroprotective agent should be administered in a dose to achieve a serum or intravitreal concentration of 0.01 nM to 50 nM. Preferably the neuroprotective agent is administered prior to injury to the nerve, but can be administered injury has occurred with lessened effect.

Conventional modes of administration and standard dosage regimens of protective agents, e.g. MK-801, can be used. Optimal dosages for coadministration of a drug, e.g. an IOP-lowering drug, with a neuroprotective agent can be determined using methods known in the art. Dosages of neuroprotective agents may be adjusted to the individual patient based on the dosage of the drug with which the agent is coadministered and the response of the patient to the treatment regimen. The protective agent may be administered to the patient at one time or over a series of treatments.

An agent that cannot pass the blood/brain barrier, e.g. MK-801, may be administered locally, e.g. intravitreally by intrabulbar injection, or intrathecally. Agents which are capable of crossing the blood/brain barrier, e.g. AGN191103 can be administered systemically, e.g., orally, or intravenously, or by injection.

The composition used in these therapies may also be in a variety of forms. These include, for example, solid, semi-solid, and liquid dosage forms, such as tablets, pills, powders, liquid solution or suspension, liposomes, suppositories, injectable and infusible solutions. The compositions also preferably include conventional pharmaceutically acceptable carriers which are known those of skill in the art.

The following non-limiting examples describe assays and measurements used in 1) determining protection of nerve cells from glutamate induced toxicity and 2) methods of determining neural protection conferred by neuroprotective agents in a nerve crush model of mechanical injury.

EXAMPLE 1

Experimental Procedure for Measuring Neural Protection in a Model of Glutamate Induced Excitotoxic Effects on Nerve Cells Low-density rat hippocampal neuronal cultures were prepared by the procedure of Goslin and Banker. Coverslips were cleaned and sterilized in porcelain racks in such a way that they did not stick to one another (Cohen cover glass staining racks, Thomas Scientific). Coverslips (13 mm) were placed in staining racks, rinsed in distilled water (four rinses, 1 min. each) to remove dust and transferred to concentrated $HNO_3$ for 36 hours. Coverslips were rinsed in distilled water (four changes over 3 hours) and sterilized with dry heat (overnight at 225° C.). The coverslips were transferred to 24-well dishes, one coverslip per well. To support the coverslips above the glia during coculturing, paraffin dots were placed on dishes, and UV irradiation (30 min.) was applied before the coverslips were introduced. One mg/mL of poly-L-lysine hydrobromide (PLL) (Sigma) (MW 30,000–70,000) was dissolved in borate buffer (0.1M, pH 8.5), filtered, sterilized and used to cover each coverslip overnight. The PLL was removed, coverslips were rinsed in distilled water (two washes, 2 hrs. each), plating medium [Eagle's MEM with Earle's salts containing extra glucose (600 mg/L) and 10% horse serum] was added and the dishes were stored in an incubator. Astroglial cultures were prepared from the brains of neonatal rats by a method similar to that described by Levinson and Mc Carthy, except that they were plated at a lower density so that they contained predominantly type 1 astroglia. $10^5$ cells were plated in each well. Glial cultures were red with plating medium twice a week and were used after reaching confluence, about 2 weeks after plating. One day before use, the plating medium was removed, neuronal maintenance medium (MEM containing N2 supplements) was added, and incubation continued. $3 \times 10^4$ of viable rat hippocampal nerves (E18 embryos) were plated on the PLL-treated coverslips kept in plating medium. After 3–4 hrs, when most of the neurons were attached, the coverslips were transferred to the dishes containing the glial cell in maintenance medium in such a way that the neuronal side was facing the glia, which support neuronal survival and development. To reduce glial proliferation, cytosine arabinoside (1-b-D-arabinofuranosylcytosine)(Calbiochem)($5 \times 10M$ final concentration) was added to the cultures 2 days after plating. At day 6 in culture, cells were treated with 1 mM glutamine or with glutamate together with either AGN-191103—0.1 nM (MW=200) or MK-801—10 nM (2–3 coverslips were used to each treatment).

After 24 hrs. of incubation, cells were stained with trypan blue. Live and dead neurons were counted from randomly selected culture fields (5 fields from each coverslip). Percentage of dead cells was calculated.

EXAMPLE 2

Procedure for Nerve Crush Injury and Measurements of Compound Action Potentials (CAP) Subsequent to Injury

Part A

Metabolic Measurements

Animal utilization was according to the ARVO Resolution on the use of animals in research. Male Sprague-Dawley (SPD) rats weighing 300–400 g were anesthetized with sodium pentobarbitone (intraperitoneally, 35 mg/kg). A cannula was introduced into the trachea for artificial ventilation when required. With the animal's head held in place by a head holder, a lateral canthotomy was performed under a binocular operating microscope and the conjunctiva was incised lateral to the cornea. After separation of the retractor bulbi muscles, the optic nerve was identified and a length of 3 0 3.5 mm was exposed near the eyeball by blunt dissection. The dura was left intact and care was taken not to injure the nerve. The first part of a light guide holder (see below) was inserted under the optic nerve and the nerve was gently eased into the light guide canal. The second part was then fixed in place in such a way that the light guide was located on the surface of the optic nerve 1 mm from the site at which the injury was to be administered.

Surface Fluorometry-Reflectometry

Monitoring of the intramitonchodrial NADH redox state was based on fluorescence of NADH at 366 nm, resulting in the emission of blue light with a peak intensity at 450 nm, which is unlike its oxidized form, NAD+, which lacks this fluorescence. The source of the 366 nm excitation is a 100-W air-cooled mercury lamp equipped with a strong 366-nm filter (Corning 5860 (7–37) plus 9782 (4–96)). A flexible Y-shaped bundle of optic fibers (light guide) is used to transmit the light to and from the optic nerve, thus making in vivo measurements technically feasible. Excitation light is transmitted through the bundle of excitation fibers to the nerve. The light emitted from the nerve, after being transmitted through a second bundle of fibers, is split in a ration of 90:10 for measurement of the fluorescent light (90%) at 450 nm and the reflected light (10%) at 366 nm by two photomultipliers connected to a one-channel direct current fluorometer-reflectometer. In order to minimize variations among animals, standard signal calibration procedures were applied at the start of the recordings.

Changes in the fluorescence and reflectance signals during the experiment are calculated relative to the calibrated signals. This type of calibration, although not absolute, has nevertheless been found to yield reliable and reproducible results from various animals and among different laboratories.

Changes in reflected light were correlated with changes in tissue absorption caused by hemodynamic effects and movements of the optic nerve secondary to alteration in arterial blood pressure and nerve volume. The fluorescence measurements are found to be adequately corrected for NADH redox state measurements by subtraction of the reflected light (366 nm) from the fluorescent light (1:1 ratio) to obtain the corrected fluorescence signal.

Metabolic Measurements

Animals which were still anesthetized were allowed to recover for 30 min. from the surgical procedures described above and were then exposed to anoxic and hyperoxic conditions. An anoxic state was achieved by having the rat breathe in an atmosphere of 100% nitrogen for 2 min., after which it was returned to air. Whenever animals did not return spontaneously to normal breathing, they were ventilated by blowing twice into the trachea. A hyperoxic state was induced by having the animal breathe 100% oxygen for 6–10 min. In order to evaluate the metabolic activity of the optic nerve, the relative changes in reflected and fluorescent light intensities in response to anoxia and to hyperoxia were measured before and after crush injury.

Experimental Protocol For Metabolic Measurements

Using calibrated cross-action forceps, a well-calibrated moderate crush injury was inflicted to the nerve between the eye and the light guide holder at a pressure corresponding to 120 g for 30 sec.

Part B

Physiological Measurements

Experimental setup for recording compound action potential (CAP): Prior to removal of optic nerves for electrophysiological measurement, the rats were deeply anesthetized with 70 mg/kg pentobarbitone. The skin was removed from the skull and the optic nerves were detached from the eyeballs. Subtotal decapitation was performed and the skull was opened with a rongeur. The cerebrum was displaced laterally, exposing the intracranial portion of the optic nerve. Dissection at the level of the chiasm enabled removal of the whole length of the nerve, which was transferred to vials containing fresh, cold Krebs solution, consisting of: NaCl (125 mM), KCl (5 mM), $KH_2PO_4$ (1.2 mM), $NaHCO_3$ (26 mM), $MgSO_4$ (0.6 mM), $CaCl_2$ (24 mM), D-glucose (11 mM), aerated with 95% $O_2$ and 5% $CO_2$. The nerves were kept in this solution, in which electrical activity remained stable for at least 3–4 h. After 1 h of recovery, nerves were immersed in Krebs solution at 37° C. Electrophysiological recording were obtained from the nerve distal to the crush lesion, since the nerves were too small to allow measurement on both sides of the crush. The nerve ends were then connected to two suction Ag—AgCl electrodes immersed in the bathing solution. The stimulating pulse was applied through the electrode at the proximal end and the action potential was recorded by the distal electrode. A Grass SD9 stimulator was used for electrical stimulation (2 V, 50 µs). The signal was transmitted to a Medelec PA63 preamplifier and thence to a Medelec MS7 electromyograph and AA7T amplifier. The solution, stimulator and amplifier had a common ground. The maximum amplitude of eight averaged CAPs was recorded and photographed with a Polaroid camera. The left nerves (uninjured) were used to measure the reference values of normal nerves and to calibrate the crush forceps.

Recording of Visual Evoked Potential (VEP) Response

Injured drug-treated rats were examined in 2 weeks after the injury for assessment of their functional recovery. In this set of experiments, the pattern of filed potentials in response to light stimulation was recorded from the primary visual cortex. The potential evoked by the light originates in the retina and is propagated along the surviving axons to reach their final target, the visual cortex. Only those axons that survived the primary and secondary degenerative processes are capable of conducting an action potential. A comparative analysis of the pattern of field potentials in treated and untreated animals will reveal the effect of the treatment on axonal survival.

Anesthetized rats (Rumpon, Ketalar) were placed in a small animal sterotaxic instrument. After exposure of the skull, two holes were drilled with a cylindrical drill bit, with the dura kept intact to minimize cortical damage. One hole, drilled above the nasal bone, was used as a reference point. The second hole was in the area OC1 with the coordinates Bregma # 8 mm, lateral # 3 mm. A gold contact pin connected to a screw was used as the electrode, which was screwed into the holes and glued by acrylic cement to the skull. The field potential was evoked by stroboscopic stimulation, with an average of 90 sweeps per minute. The flash-evoked potential was analyzed by the use of the Lab View data acquisition and management system. The field potentials were digitized and stored for off-line analysis.

Part C

Measurement of Effects of Drug Tests for Neural Protective Properties

The first set of experiments involved metabolic measurements. Each drug was injected intraperitoneally at several different concentrations. Each drug was tested in a group of 8 animals, together with 8 controls (injured animals treated with the buffer vehicle). In each case, metabolic measurements were obtained on-line before injury, 0.5 h after injury and every hour for 4–6 h thereafter. The data obtained were analyzed by ANOVA.

Measurement of Long Term Effects

Physiological Activities

CAPS

Immediately after injury, the drug to be tested was injected into 10 animals, and 10 control animals were injected with vehicle. Two weeks later the CAPs of each nerve were recorded in vitro, using suction electrodes. The contralateral side was used as an internal control. The results indicated whether the examined drug had any potential effects on the rescue of spared axons and/or slowing of degeneration. Positive results led to efforts at determining the optimal dosage for each promising drug.

VEP Response

Electrodes were implanted in the cortex of naive SPD rats in two age- and sex-matched groups. Immediately after implantation, the VEP response was recorded from the left side while a light was flashed into the right eye, with the left eye covered. A well-controlled crush injury was then inflicted on the optic nerve and the drug was immediately administered at the previously determined optimal dosage. Control animals were handled in the same way except vehicle was administered rather than drug. The VEP response for each animal was recorded 1 day, 1 week, 2 weeks and 4 weeks after operation.

While this invention has been described with respect to various specific examples and embodiments, it is to be understood that the invention is not limited thereby and should only be construed by interpretation of the scope of the appended claims.

What is claimed is:

1. A method of protecting the retinal or optic nerve cells in a mammal suffering a noxious action or at risk of experiencing a noxious action on said nerve cells comprising administering to said mammal an amount and dosage regimen of a compound of formula I effective to inhibit or prevent nerve cell injury or death

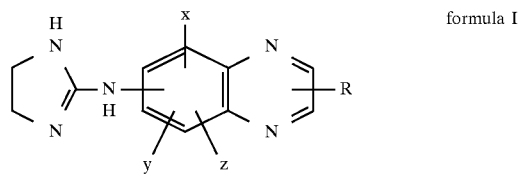

formula I wherein the 2-imidazolin-2-ylamino group is in either the 5- or 6-position of the quinoxaline nucleus; x, y and z are in any of the remaining 5-, 6-, 7- or 8-positions and are selected from hydrogen, halogen, lower alkyl, lower alkoxy or trifluoromethyl; and R is an optional substituent in either the 2- or 3-position of the quinoxaline nucleus and may be hydrogen, lower alkyl or lower alkoxy, or pharmaceutically acceptable salts thereof and mixtures thereof.

2. The method of claim 1 wherein the noxious action is diabetic retinopathy.

3. The method of claim 1 wherein the noxious action is non-glaucoma tous ischemia.

4. The method of claim 1 wherein the noxious action is microangiopathic in nature and is a symptom of the disease chosen from the group consisting of polyarteritis nodosa, giant cell angitis, aortitis syndrome and systemic lupus erythematosus.

5. The method of claim 1 wherein oral administration is used to supply the compound to the mammal systemically.

6. The method of claim 5 wherein the amount of the compound administered is from 5–15 mg/kg.

7. The method of claim 1 wherein intrabulbar injection in the eye is used to supply the compound to the mammal.

8. The method of claim 1 wherein parenteral administration is used to supply the compound to the mammal systemically.

9. The method of claim 1 wherein intramuscular injection is used to supply the compound to the mammal systemically.

10. The method of claim 1 wherein the compound of formula I has the 2-imidazolin-2-ylamino group at the 6-position of the quinoxaline ring, y and z are both hydrogen and located at the 7- and 8-positions and x is at the 5-position of the quinoxaline ring.

11. The method of claim 1 wherein the compound of formula I is

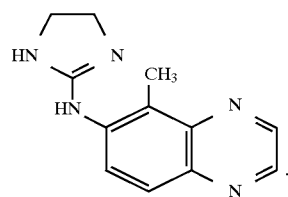

12. The method of claim 1 wherein the compound of formula I is

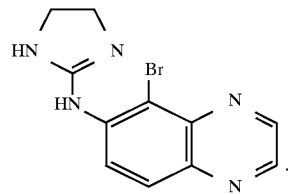

13. The method of claim 1 wherein the compound of formula I is

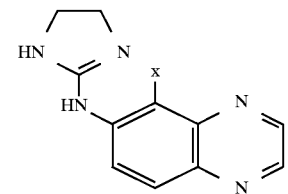

wherein x is as defined in claim 1 and the noxious action is diabetic retinopathy.

14. The method of claim 1 wherein the compound of formula I is

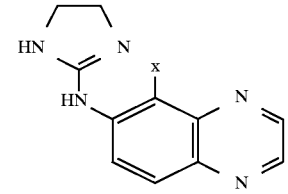

wherein x is as defined in claim 1 and the noxious action is non-glaucomatous ischemia.

15. The method of claim 1 wherein the compound of formula I is

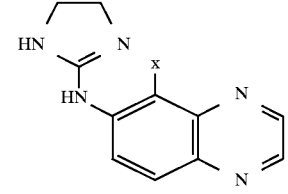

wherein x is as defined in claim 1 and the noxious action is microangiopathic in nature and is chosen from the group consisting of polyarteritis nodosa, giant cell angitis, aortitis syndrome and systemic lupus erythematosus.

* * * * *